(12) United States Patent
Kim et al.

(10) Patent No.: US 8,495,907 B2
(45) Date of Patent: Jul. 30, 2013

(54) METHOD AND APPARATUS FOR MEASURING DRYING TIME OF QUICK WET AND DRIED FABRICS

(75) Inventors: You kyum Kim, Seoul (KR); Yea suk Yoon, Seoul (KR)

(73) Assignee: Fiti Testing & Research Institute, Seoul (KR)

( * ) Notice: Subject to any disclaimer, the term of this patent is extended or adjusted under 35 U.S.C. 154(b) by 433 days.

(21) Appl. No.: 12/666,795

(22) PCT Filed: Jun. 25, 2008

(86) PCT No.: PCT/KR2008/003659
§ 371 (c)(1),
(2), (4) Date: Dec. 24, 2009

(87) PCT Pub. No.: WO2009/002099
PCT Pub. Date: Dec. 31, 2008

(65) Prior Publication Data
US 2010/0326221 A1   Dec. 30, 2010

(30) Foreign Application Priority Data
Jun. 25, 2007   (KR) .................. 10-2007-0062404

(51) Int. Cl.
*G01N 25/58* (2006.01)
(52) U.S. Cl.
USPC ............................................. 73/73; 73/865.5
(58) Field of Classification Search
USPC ......................................... 73/73, 865.6, 866
See application file for complete search history.

(56) References Cited

U.S. PATENT DOCUMENTS

| | | | | |
|---|---|---|---|---|
| 3,050,418 | A | * | 8/1962 | Mendelsohn et al. .......... 525/58 |
| 4,312,219 | A | * | 1/1982 | Lee et al. ......................... 73/76 |
| 5,385,081 | A | | 1/1995 | Sneddon |
| 7,458,288 | B2 | * | 12/2008 | Polegato Moretti ......... 73/865.6 |
| 2004/0177529 | A1 | | 9/2004 | Kim et al. |
| 2005/0050763 | A1 | | 3/2005 | Park |

FOREIGN PATENT DOCUMENTS

| | | |
|---|---|---|
| DE | 971397 | 1/1959 |
| DE | 3750848 | 5/1995 |
| DE | 69917329 | 5/2005 |

OTHER PUBLICATIONS

International Search Report for PCT/KR2008/003659 mailed Oct. 22, 2008.

\* cited by examiner

*Primary Examiner* — Hezron E Williams
*Assistant Examiner* — Paul West
(74) *Attorney, Agent, or Firm* — Christopher Paul Mitchell

(57) ABSTRACT

Disclosed is a method for measuring the drying time of a moisture-wicking and quick-drying material that enables convenient and precise measurement of the drying time of the material by creating an environment similar to the skin surface of a human body wearing clothes. The method includes: creating a temperature and humidity state similar to a condition in which sweat of a human body is shed on the bottom surface of a test material; blowing wind to the upper surface of the test material at a speed similar to a speed at which a human being is walking; dropping distilled water to the upper surface of the test material with the temperature and humidity state and the wind speed being maintained constant; and measuring the drying time of the test material with the distilled water having been dropped to the upper surface of the test material.

4 Claims, 2 Drawing Sheets

[Fig. 1]
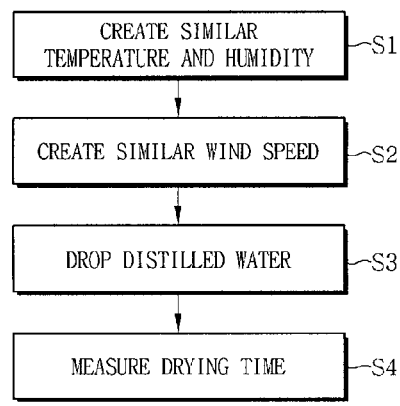
[Fig. 2]
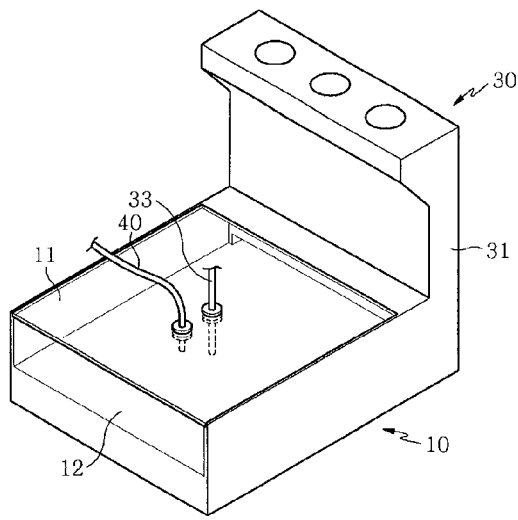
[Fig. 3]
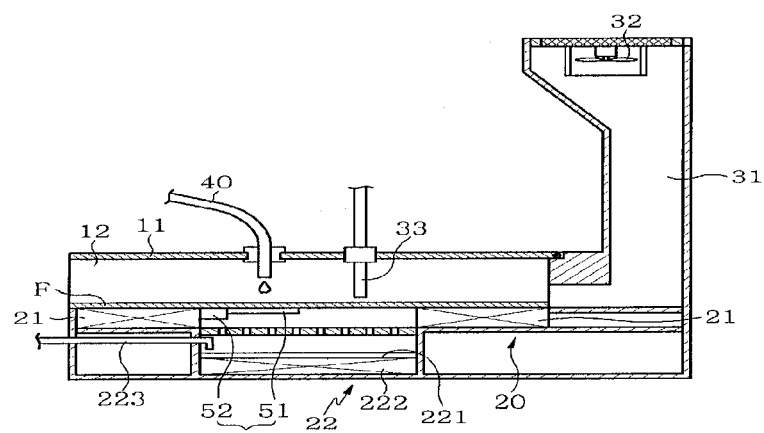

[Fig. 4]
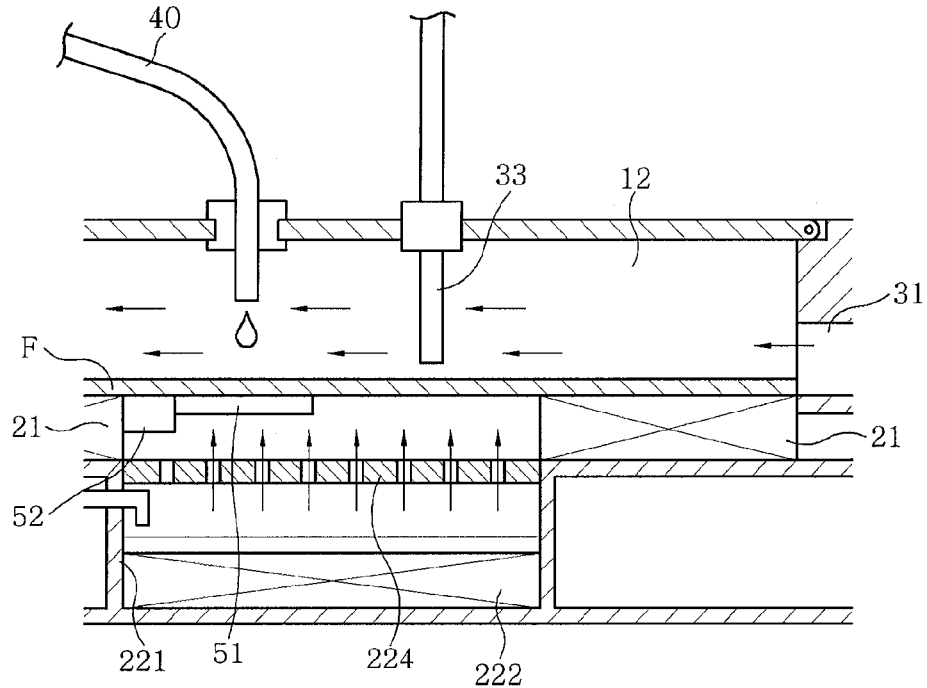
[Fig. 5]
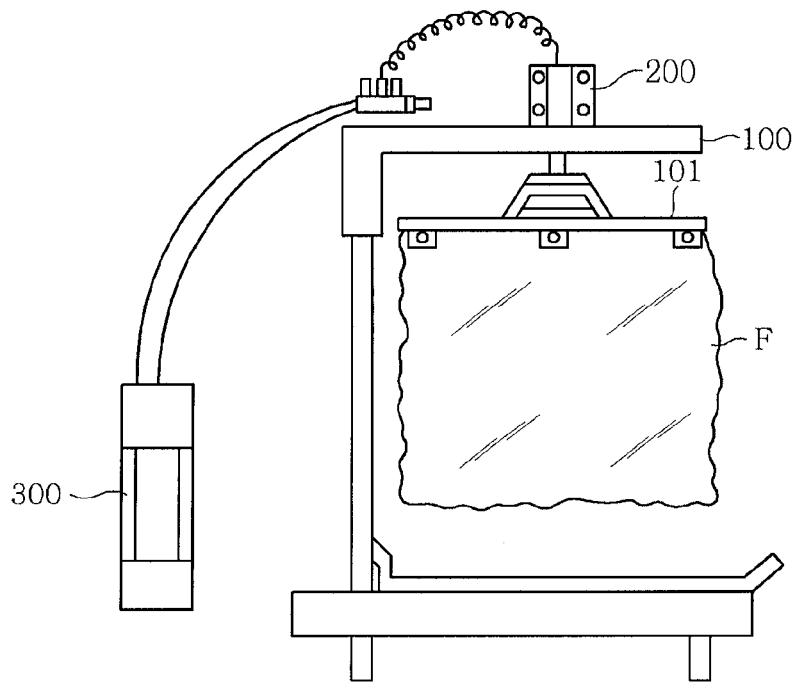

METHOD AND APPARATUS FOR MEASURING DRYING TIME OF QUICK WET AND DRIED FABRICS

Related Applications

This application is a 371 application of International Application No. PCT/KR2008/003659, filed Jun. 25, 2008, which in turn claims priority from Korean Patent Application No. 10-2007-0062404, filed Jun. 25, 2007, both of which are incorporated herein by reference in their entireties.

TECHNICAL FIELD

The present invention relates generally to a method and an apparatus for measuring the drying time of quick wet and dried fabrics and, more particularly, to a method and an apparatus for measuring the drying time of a moisture-wicking and quick-drying material that enable convenient and precise measurement of the drying time of the material by creating an environment similar to the skin surface of a human body wearing clothes.

BACKGROUND ART

In general, moisture-wicking and quick-drying materials refer to fiber materials for sports and leisure which wick sweat shedding from a human body and quickly dry the wicked sweat.

Recently, such moisture-wicking and quick-drying materials are being rapidly developed due to their utility, and, as a result, test equipment for the drying efficiencies of such materials is also being urgently required.

As illustrated in FIG. 5, a drying time measuring apparatus according to the prior art includes a stand 100 having a suspension clip 101, a strain gauge 200 connected to the suspension clip 101, and a strain meter 300 recording values of the strain gauges 200.

The drying time measuring apparatus according to the prior art measures the drying time of a sample material F containing moisture through a change of the tension state measured by the strain gauge with the sample material F being suspended on the suspension clip 101.

However, the drying time measuring apparatus according to the prior art has the following disadvantages.

Although it is necessary to accurately measure the moisture wicking and drying efficiency of a moisture-wicking and quick-drying material, the drying time measuring apparatus according to the prior art cannot create an environment similar to a human body, in which case it is difficult to accurately measure the drying time of sweat in the state similar to a human body by measuring only a naturally dried state.

DISCLOSURE

Technical Problem

The present invention has been made in view of the above problems, and the present invention provides a method and an apparatus for measuring the drying time of a moisture-wicking and quick-drying material that enable convenient and precise measurement of the drying time of the material by creating an environment similar to the skin surface of a human body wearing clothes.

The present invention also provides a method and an apparatus for measuring the drying time of a moisture-wicking and quick-drying material that enable more accurate measurement of the drying time of the material through measurement of moisture permeability of the material.

The present invention also provides a method and an apparatus for measuring the drying time of a moisture-wicking and quick-drying material that enable easy creation of temperature and humidity similar to those of a skin surface of a human body wearing clothes using a simple structure.

Technical Solution

In accordance of an exemplary embodiment of the present invention, there is provided a method for measuring the drying time of a moisture-wicking and quick-drying material, the method including: creating a temperature and humidity state similar to a condition in which sweat of a human body is shed on the bottom surface of a test material; blowing wind to the upper surface of the test material at a speed similar to a speed at which a human being is walking; dropping distilled water to the upper surface of the test material with the temperature and humidity state and the wind speed being maintained constant; and measuring the drying time of the test material with the distilled water having been dropped to the upper surface of the test material.

The drying time of the test material is measured through measurement of the moisture permeability of the test material.

In accordance with another exemplary embodiment of the present invention, there is provided an apparatus for measuring the drying time of a moisture-wicking and quick-drying material, the method including: a body an opened upper surface of which is covered by a transparent cover so as to define an opened chamber at an upper portion thereof so that a test material is disposed at a lower portion of the chamber; a temperature and humidity creating unit installed in the body under the chamber to create temperature and humidity similar to those of a human body; a wind speed creating unit including a blowing channel formed on one side of the body and communicated with the chamber and a blower installed inside the blowing channel, the wind speed creating unit horizontally blowing wind along the chamber; a distilled water dropping pipe mounted to the cover so as to pass through the cover to drop distilled water to the test material disposed on the bottom surface of the chamber; and a drying time measuring unit measuring the drying time of the distilled water dropping to the test material.

The drying time measuring unit includes a moisture permeability measurer installed in the body to measure the moisture permeability of the test material and a timer measuring a time period from a time point when the distilled water drops to a time point when the moisture permeability of the test material returns to a value before the distilled water drops using data input from the moisture permeability measurer.

The temperature and humidity creating unit includes a pair of hot plates installed on both sides of the body at lower portions of the chamber to generate heat and a vapor generator disposed between the hot plates to generate vapor.

The vapor generator includes a vessel disposed inside the body between the hot plates and the upper side of which is opened, a heater installed inside the vessel to heat water, a water supply pipe connected to the vessel to supply water to the vessel from outside, and a punched hole plate mounted to the opened upper surface of the vessel to pass vapor therethrough.

The wind speed creating unit further includes a wind speed detector mounted to the cover so as to pass through the cover to detect wind speed over the bottom surface of the chamber.

ADVANTAGEOUS EFFECTS

As mentioned above, according to the present invention, the drying time of a moisture-wicking and quick-drying material can be conveniently and precisely measured by creating an environment similar to a skin surface of a human body wearing clothes.

Further, the drying time of the material can be more precisely measured by measuring the moisture permeability of the material.

Furthermore, an apparatus for measuring the drying time of a moisture-wicking and quick-drying material can be conveniently manufactured and installed using a simple structure and temperature and pressure similar to a skin surface of a human body wearing clothes can be easily created.

DESCRIPTION OF DRAWINGS

The objects, features and advantages of the present invention will be more apparent from the following detailed description in conjunction with the accompanying drawings, in which:

FIG. 1 is a block diagram illustrating a measuring method according to an embodiment of the present invention.

FIG. 2 is a perspective view schematically illustrating a measuring apparatus according to an embodiment of the present invention.

FIG. 3 is a schematic side sectional view of FIG. 2.

FIG. 4 is a partially enlarged side sectional view illustrating an operational state of the measuring device of FIG. 2.

FIG. 5 is a front view illustrating an example of a measuring apparatus according to the prior art.

DESCRIPTION OF MAIN REFERENCE NUMERALS

10: Body
11: Cover
12: Chamber
20: Temperature and humidity creating unit
21: Hot plate
22: Vapor generator
30: Wind speed creating unit
31: Blowing channel
32: Blower
40: Distilled water dropping unit
50: Drying time measuring unit
51: Moisture permeability measurer

BEST MODE

Hereinafter, exemplary embodiments of the present invention will be described in detail with reference to the accompanying drawings.

FIG. 1 is a block diagram illustrating a measuring method according to an embodiment of the present invention.

As illustrated in FIG. 1, a method for measuring a drying time of a moisture-wicking and quick-drying material includes a similar temperature and humidity creating step S1 of creating temperature and humidity similar to those of a human body, a similar wind speed creating step S2 of creating a wind speed similar to a speed at which a human being is walking, a distilled water dropping step S3 of dropping distilled water to the test material, and a drying time measuring step S4 of measuring the drying time of the distilled water.

The similar temperature and humidity creating step S1 refers to a step of creating temperature and humidity similar to a condition in which sweat of a human body is shed on the bottom surface of a test material.

In step S1, temperature and humidity similar to an external condition of a human body is created to make the state of the test material similar to a state in which the human body wears the test material, and the measurement of the drying speed of the test material is carried out preferably at a humidity of 40% and a temperature of 35 degrees that are similar to the external temperature and humidity on a skin surface of the human body.

The similar wind speed creating step S2 refers to a step of blowing wind to the upper surface of the test material at a speed similar to a speed at which a human being is walking.

In step S2, a state in which a human body wears the test material becomes more accurate by adding a condition in which a human being is walking, and the wind speed is preferably 1 m/sec.

The distilled water dropping step S3 refers to a step of dropping distilled water to the upper surface of the test material with the temperature and humidity state and the wind speed being determined.

In step S3, a state in which sweat is shed to the test material is created by dropping the distilled water, and the amount of distilled water is preferably 5 ml.

The drying time measuring step S4 refers to a step of measuring the drying time of the test material with the distilled water having been dropped to the upper surface of the test material.

The measurement of drying time is preferably carried out through measurement of humidity permeability, and it is because the drying time may be accurately measured even when vapor is continuously shed from the skin of a human body with the moisture-wicking and quick-drying material absorbing sweat.

The measurement of drying time through change of moisture permeability is carried out by measuring a lapse time period from a time point when the distilled water drops to a time point when the moisture permeability of the test material reaches a value before the distilled water drops, after measuring a moisture permeability of the test material before the distilled water drops.

FIG. 2 is a perspective view schematically illustrating a measuring apparatus according to an embodiment of the present invention, and FIG. 3 is a schematic side sectional view of FIG. 2.

As illustrated in FIGS. 2 and 3, the apparatus for measuring the drying time of a moisture-wicking and quick-drying material includes a body in which a test material F is disposed, a temperature and humidity creating unit 20 installed in the body 10 to create an environment similar to external temperature and humidity of a human body, a wind speed creating unit 30 installed in the body 10 to create wind speed, a distilled water dropping pipe 40 dropping distilled water to the test material F, and a drying time measuring unit 50 measuring the drying time of the test material F.

An opened upper surface of the body 10 is covered by a transparent cover 11 so as to define an opened chamber 12 at an upper portion thereof so that a test material F is disposed at a lower portion of the chamber 12.

A temperature and humidity creating unit 20 is installed in the body 10 under the chamber 12 to create temperature and humidity similar to those of a human body.

The temperature and humidity creating unit 20 includes a pair of hot plates 21 installed on both sides of the body 10 at lower portions of the chamber 12 to generate heat and a vapor generator 22 disposed between the hot plates 21 to generate vapor.

The hot plates 21 create a condition similar to heat generated from a human body and the vapor generator 22 creates a condition similar to one in which sweat is evaporated from a human body.

The vapor generator 22 includes a vessel 221 disposed inside the body 10 between the hot plates 21 and the upper side of which is opened, a heater 222 installed inside the vessel 221 to heat water, a water supply pipe 223 connected to the vessel 221 to supply water to the vessel 211 from outside, and a punched hole plate 224 mounted to the opened upper surface of the vessel 221 to pass vapor therethrough.

The water introduced into a vessel 221 through the water supply pipe 223 is heated by the heater 222 to be evaporated to vapor, which in turn rises through the punched hole plate 223 to create humidity suitable for the test material F.

The wind speed creating unit 30 horizontally blows wind along the chamber 12, and creates wind speed similar to one at which a human being is walking.

The wind speed creating unit 30 includes a blowing channel 31 formed on one side of the body 10 and communicated with the chamber 12 and a blower 32 installed inside the blowing channel 31.

The wind speed creating unit 30 further includes a wind speed detector 33 mounted to the cover 11 so as to pass through the cover 11 to detect wind speed over the bottom surface of the chamber 12. The wind speed detector 33 measures wind speed created by the blower 32 at a lower portion of the chamber 12, and then controls the operation of the blower 32 according to a detected value, maintaining a specific speed.

The distilled water dropping pipe 40 is mounted to the cover 11 so as to pass through the cover 11 to drop distilled water to the test material F disposed on the bottom surface of the chamber 12. The dropping distilled water functions as sweat absorbed by the test material F.

The drying time measuring unit 50 measures the drying time of the distilled water dropping to the test material F, and includes a moisture permeability measurer 51 installed in the body 10 to measure the moisture permeability of the test material F and a timer 52 measuring a time period from a time point when the distilled water drops to a time point when the moisture permeability of the test material F returns to a value before the distilled water drops using data input from the moisture permeability measurer 51.

FIG. 4 is a partially enlarged side sectional view illustrating an operational state of the measuring device of FIG. 2.

As illustrated in FIG. 4, the temperature similar to that of a human body is created by operating the hot plates 21 with the test material F being disposed in the chamber 12 and the humidity similar to that external to a human body by raising vapor through the punched hole plate 224 by operating the heater 222 to heat the water inside the vessel.

The wind speed similar to that at which a human being is walking is created at a lower portion of the chamber 12 through the blowing channel 31 by operating a blower (not shown) with the temperature and humidity being created at the same time. Then, the wind speed detector 33 detects wind speed to maintain the wind speed constant.

One drop of distilled water falls to the upper surface of the test material F through the distilled water dropping pipe 40 with the temperature, humidity, and wind speed being maintained constant.

The distilled water dropping to the upper surface of the test material F is absorbed by the test material F so as to permeate into the test material F, in which case the drying time of the test material F is measured through the moisture permeability measurer 51 and the timer 52.

[Industrial Applicability]

The present invention relates generally to a method and an apparatus for measuring the drying time of a moisture-wicking and quick-drying material and enables convenient and precise measurement of the drying time of the material by creating an environment similar to the skin surface of a human body wearing clothes.

The invention claimed is:

1. An apparatus for measuring the drying time of a moisture-wicking and quick-drying material, the apparatus comprising:
   a body an opened upper surface of which is covered by a transparent cover so as to define an opened chamber at an upper portion thereof so that a test material is disposed at a lower portion of the chamber;
   a temperature and humidity creating unit installed in the body under the chamber to create temperature and humidity similar to those of a human body; a wind speed creating unit including a blowing channel formed on one side of the body (10) and communicated with the chamber and a blower installed inside the blowing channel, the wind speed creating unit horizontally blowing wind along the chamber;
   a distilled water dropping pipe mounted to the cover so as to pass through the cover to drop distilled water to the test material (disposed on the bottom surface of the chamber; and
   a drying time measuring unit measuring the drying time of the distilled water dropping to the test material.

2. The apparatus of claim 1, wherein the temperature and humidity creating unit includes a pair of hot plates installed on both sides of the body at lower portions of the chamber to generate heat and a vapor generator disposed between the hot plates to generate vapor.

3. The apparatus of claim 2, wherein the vapor generator includes a vessel disposed inside the body between the hot plates and the upper side of which is opened, a heater installed inside the vessel to heat water, a water supply pipe connected to the vessel to supply water to the vessel from outside, and a punched hole plate) mounted to the opened upper surface of the vessel to pass vapor therethrough.

4. The apparatus of claim 1, wherein the wind speed creating unit further includes a wind speed detector mounted to the cover so as to pass through the cover to detect wind speed over the bottom surface of the chamber.

* * * * *